Figure 1:
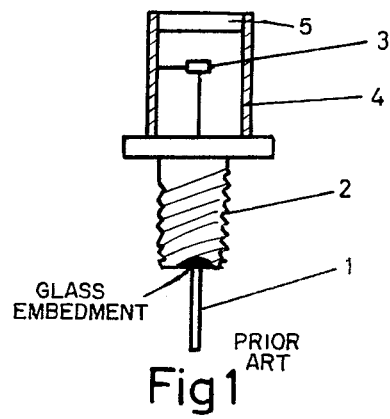

United States Patent [19]
Andersson

[11] 3,955,176
[45] May 4, 1976

[54] COLD TRAP FOR LASER DIODES
[75] Inventor: Kenth Yngve Andersson, Karlskoga, Sweden
[73] Assignee: AB Bofors, Bofors, Sweden
[22] Filed: Sept. 4, 1974
[21] Appl. No.: 503,196

[30] Foreign Application Priority Data
Sept. 4, 1973 Sweden............................ 7312001

[52] U.S. Cl. ................................. 357/81; 313/17
[51] Int. Cl.² ........................................ H01L 23/02
[58] Field of Search................................ 357/17, 81

[56] References Cited
UNITED STATES PATENTS
3,209,218  9/1965  Zielasek et al................... 357/81 X
3,222,580  12/1965  Curll .................................. 357/81
3,239,003  3/1966  Boudette et al. ................. 357/81 X Primary Examiner—R. V. Rolinec
Assistant Examiner—Darwin R. Hostetter
Attorney, Agent, or Firm—Pollock, Vande Sande & Priddy

[57] ABSTRACT

A laser diode is provided with a casing that encloses a light-emitting crystal. The casing includes a transparent member through which the light passes. A portion of the diode is positioned within a holder and means is provided for cooling the diode. To reduce condensation of moisture which is present within the holder, upon the transparent member, a sleeve formed of a thermally high conductor material such as copper is placed about the casing with close physical contact therebetween.

5 Claims, 3 Drawing Figures

COLD TRAP FOR LASER DIODES

The present invention relates to a so-called cold trap for laser diodes (solid state lamps).

In order to be able to utilize the properties of a light-emitting diode optimally, it is necessary that the diode be cooled. This can be accomplished by allowing the shaft of the diode to come into contact with a cooling liquid, for cooling down to −40°C. This low temperature corresponds to the dew-point of a water vapour concentration of 0.1 mg/l (corresponding to 0.6 % relative humidity at +25°C). It is only with very great difficulty that such a dry climate can be achieved for the diode. If said air humidity is exceeded, moisture is precipitated on the diode, i.e. also on the glass, which involves a diffusion of the light and less possibility of utilizing the light-emitting effect.

In previously known devices comprising cooled laser diodes, various methods have therefore been used for drying the air around the diode. Such a drying of the air requires drying agents such as phosphours pentoxide or magnesium perchlorate, which are difficult to handle because of their considerable absorption capability. These drying agents are moreover characterized by their being consumed unless the space around the diode is absolutely tightly sealed.

In another previously known device, dry nitrogen is used for filling or flowing through the space surrounding the diode. However, such a device is large and impractical to handle. The possibility of allowing nitrogen drying to be included in a light, portable system is non-existent.

The purpose of the present invention is to achieve a simple cold trap where the air humidity is precipitated and which entirely protects the glass from moisture, without impeding the outflow of light.

This is achieved according to the invention by a sleeve made of material with good thermal conductivity which is applied with good thermal contact to the diode casing.

Figure 2:
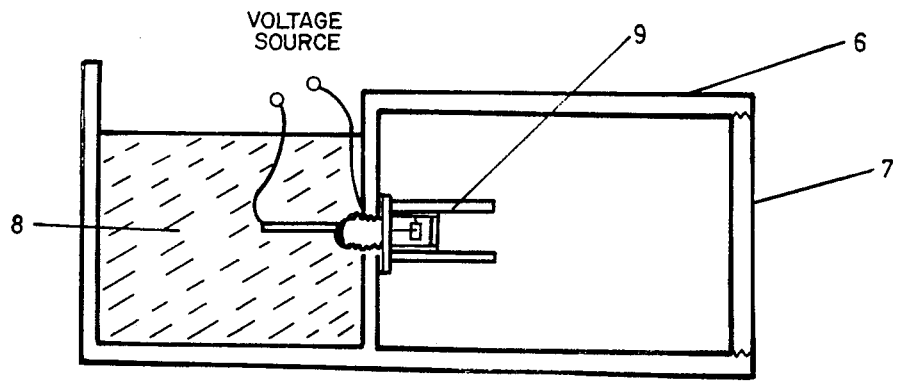
Figure 3:
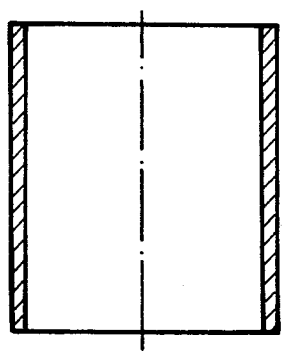

The invention will be described in more detail in the following, with reference to the attached drawing, in which FIG. 1 shows the construction of a conventional laser diode, FIG. 2 shows the cold trap mounted on a diode, and FIG. 3 shows the embodiment of the actual cold trap.

FIG. 1 shows a laser diode which comprises an anode 1 and a cathode 2, which is provided with threads and can be fitted in a fastening device. The diode also comprises a light-emitting crystal 3, which is enclosed in a casing 4, particularly made of steel, and a glass window 5 through which the light can pass.

FIG. 2 shows an appropriate device for utilizing the light-emitting effect of the diode, in which the diode is mounted in a holder 6, which also comprises a piece of glass 7. The shaft of the diode is cooled with the aid of a cooling liquid 8. On the casing of the diode, a sleeve 9, made in the form of an open cylinder, has been applied. The sleeve 9 is made of material with good thermal conductivity, and is made with an inner diameter which is approx 15 μm less than the outer diameter of the diode casing. It is then forced onto the diode casing, to give the best thermal contact. When cooled down, the temperature of the sleeve will go down faster than that of the piece of glass. According to the "cold wall principle", moisture will then be precipitated on the sleeve. The shape and position of the sleeve also tends to prevent molecules of water in a gaseous form from coming into contact with the surface of the glass.

Measurements made on a copper sleeve according to FIG. 3 show that a quantity of water of the order of 1 mg can be absorbed by the copper sleeve without any precipitation on the glass taking place. This is the water content in an air volume of approx 0.15 $dm^3$ at +25°C and 35 % relative air humidity (normal indoor environment).

Although, in the foregoing, the invention has been described in conjunction with a particular type of laser diode, where the sleeve has been forced onto the diode casing, it should be obvious that the invention can also be applied to other light-emitting diodes, and where the good thermal contact between the sleeve and the casing can be achieved also in other ways, e.g. through chemical bonding between these parts.

I claim:

1. Apparatus for use with a light-emitting diode having an anode and a cathode and a light-emitting element and a casing surrounding said light-emitting element and including a light-transparent element, said apparatus comprising in combination:
    a holder enclosing said casing,
    means for cooling said diode,
    and means for preventing the condensation onto the light-transparent element of the cooled diode the water vapour present in said holder, said means comprising a sleeve of high thermal conductivity which tightly contacts and substantially surrounds said casing except for the light transparent element thereof.

2. The combination of claim 1 wherein the portion of said casing which is contacted by said sleeve is of metal.

3. The apparatus of claim 2 wherein said sleeve is a copper sleeve.

4. The apparatus of claim 1 wherein said sleeve and said casing are both circular cylinders and said sleeve has an inner diameter which is about 15 micromillimeters less than the outer diameter of said casing.

5. The apparatus of claim 4 wherein said sleeve has an axial length greater than that of said casing.

* * * * *